US010765399B2

(12) United States Patent
Emmanouilidou et al.

(10) Patent No.: US 10,765,399 B2
(45) Date of Patent: Sep. 8, 2020

(54) PROGRAMMABLE ELECTRONIC STETHOSCOPE DEVICES, ALGORITHMS, SYSTEMS, AND METHODS

(71) Applicant: The Johns Hopkins University, Baltimore, MD (US)

(72) Inventors: Dimitra Emmanouilidou, Baltimore, MD (US); James E. West, Baltimore, MD (US); Mounya Elhilali, North Potomac, MD (US); Ian Mclane, Baltimore, MD (US)

(73) Assignee: The Johns Hopkins University, Baltimore, MD (US)

( * ) Notice: Subject to any disclaimer, the term of this patent is extended or adjusted under 35 U.S.C. 154(b) by 0 days.

(21) Appl. No.: 15/772,454

(22) PCT Filed: Oct. 31, 2016

(86) PCT No.: PCT/US2016/059752
§ 371 (c)(1),
(2) Date: Apr. 30, 2018

(87) PCT Pub. No.: WO2017/075601
PCT Pub. Date: May 4, 2017

(65) Prior Publication Data
US 2018/0317876 A1    Nov. 8, 2018

Related U.S. Application Data

(60) Provisional application No. 62/249,028, filed on Oct. 30, 2015.

(51) Int. Cl.
*A61B 7/04* (2006.01)
*G06N 20/00* (2019.01)
(Continued)

(52) U.S. Cl.
CPC .................. *A61B 7/04* (2013.01); *A61B 5/08* (2013.01); *A61B 5/7203* (2013.01);
(Continued)

(58) Field of Classification Search
CPC ........................................................ A61B 7/04
See application file for complete search history.

(56) References Cited

U.S. PATENT DOCUMENTS 5,036,857 A * 8/1991 Semmlow ............... A61B 5/024
600/493
5,539,831 A * 7/1996 Harley ..................... A61B 7/04
381/151

(Continued)

FOREIGN PATENT DOCUMENTS

EP           1774912 A1    4/2007
WO    2014/163443 A1    10/2014

OTHER PUBLICATIONS

International Search Report and Written Opinion in International Patent Publication No. PCT/US2016/059752, dated Jan. 10, 2017.
(Continued)

*Primary Examiner* — Olisa Anwah
(74) *Attorney, Agent, or Firm* — Venable LLP; Henry J. Daley

(57) ABSTRACT

A digital electronic stethoscope includes an acoustic sensor assembly that includes a body sensor portion and an ambient sensor portion, the body sensor portion being configured to make acoustically coupled contact with a subject while the ambient sensor portion is configured to face away from the body sensor portion so as to capture environmental noise proximate the body sensor portion; a signal processor and data storage system configured to communicate with the acoustic sensor assembly so as to receive detection signals therefrom, the detection signals including an auscultation signal comprising body target sound and a noise signal; and
(Continued)

an output device configured to communicate with the signal processor and data storage system to provide at least one of an output signal or information derived from the output signal. The signal processor and data storage system includes a noise reduction system that removes both stationary noise and non-stationary noise from the detection signal to provide a clean auscultation signal substantially free of distortions. The signal processor and data storage system further includes an auscultation sound classification system configured to receive the clean auscultation signal and provide a classification thereof as at least one of a normal breath sound or an abnormal breath sound.

30 Claims, 6 Drawing Sheets

(51) Int. Cl.
| | | |
|---|---|---|
| *A61B 5/00* | (2006.01) | |
| *A61B 5/08* | (2006.01) | |
| *G10K 11/178* | (2006.01) | |
| *G16H 40/63* | (2018.01) | |
| *G06N 99/00* | (2019.01) | |
| *A61B 7/00* | (2006.01) | |
| *A61B 7/02* | (2006.01) | |
| *G10L 25/51* | (2013.01) | |

(52) U.S. Cl.
CPC ............ *A61B 5/7264* (2013.01); *A61B 7/003* (2013.01); *A61B 7/026* (2013.01); *G06N 20/00* (2019.01); *G06N 99/00* (2013.01); *G10K 11/178* (2013.01); *G16H 40/63* (2018.01); *G10K 2210/116* (2013.01); *G10L 25/51* (2013.01)

(56) References Cited

U.S. PATENT DOCUMENTS

| | | | | |
|---|---|---|---|---|
| 5,812,678 | A * | 9/1998 | Scalise | A61B 7/003 381/67 |
| 2008/0013747 | A1* | 1/2008 | Tran | A61B 7/04 381/67 |
| 2009/0060215 | A1 | 3/2009 | Ocasio | |
| 2009/0316925 | A1* | 12/2009 | Eisenfeld | A61B 7/008 381/67 |
| 2010/0160807 | A1 | 6/2010 | Schmidt et al. | |
| 2012/0310115 | A1* | 12/2012 | Bedingham | A61B 7/04 600/586 |
| 2013/0041278 | A1* | 2/2013 | Bai | A61B 7/04 600/529 |
| 2013/0259240 | A1 | 10/2013 | Chang | |
| 2014/0126732 | A1* | 5/2014 | West | H04R 1/46 381/67 |
| 2016/0095571 | A1* | 4/2016 | Shams | A61B 7/04 600/586 |
| 2017/0135670 | A1* | 5/2017 | Kametani | A61B 5/08 |

OTHER PUBLICATIONS

European Search Report from corresponding European Application No. 16 861 0493.1 dated Jun. 16, 2019.
Basu et al., "A nonparametric test for stationarity based on local Fourier analysis," Acoustics, Speech and Signal, pp. 3005-3008 (2009).
Chi et al., "Multiresolution spectrotemporal analysis of complex sounds," J. Acoust. Soc. Am., 118, pp. 887-906 (2005).
Dahimene et al., "A Simple Algorithm for the Restoration of Clipped Speech Signal," Informatica, 32, pp. 183-188 (2008).
Davis, "Comparison of parametric representations for monosyllabic word recognition in continuously spoken sentences," IEEE Transactions on Acoustics, Speech and Signal Processing, 28(4), pp. 357-366 (1980).
Emmanouilidou et al., "A multiresolution analysis for detection of abnormal lung sounds," In Engineering in Medicine and Biology Society (EMBC), 2012 Annual International Conference of the IEEE, pp. 3139-3142 (Aug. 2012).
Emmanouilidou et al., "Adaptive noise suppression of pediatric lung auscultations with real applications to noisy clinical settings in developing countries," Biomedical Engineering, IEEE Transactions on, vol.PP, No. 99, pp. 1,1.
Emmanouilidou et al., "Characterization of noise contaminations in lung sound recordings," in Engineering in Medicine and Biology Society, vol. 2013, pp. 2551-2554 (2013).
Flietstra et al., "Automated analysis of crackles in patients with interstitial pulmonary fibrosis," Pulmonary medicine, 2011(2): 590506.
Flores-Tapia et al., "Heart sound cancellation based on multiscale products and linear prediction," IEEE Transactions on Biomedical Engineering, 54(2), pp. 234-243 (Feb. 2007).
Garrett et al., "Noise control challenges for auscultation on medical evacuation helicopters." Applied Acoustics, vol. 80, pp. 68-78 (Jun. 2014). Web.
Ghaderi et al., "Localizing heart sounds in respiratory signals using singular spectrum analysis," IEEE Transactions on Biomedical Engineering, 58(12), pp. 3360-3367 (Dec. 2011).
Gnitecki et al., "Qualitative and quantitative evaluation of heart sound reduction from lung sound recordings," IEEE Transactions on Biomedical Engineering on, 52(10), pp. 1788-1792 (Oct. 2005).
Groom, "The effect of background noise on cardiac auscultation." Am Heart J, 52 (5), pp. 781-790 (1956).
Guntupalli, "Validation of automatic wheeze detection in patients with obstructed airways and in healthy subjects," the Journal of Asthma: Official Journal of the Association for the Care of Asthma, 45(10), pp. 903-907, (Dec. 2008).
Gurung et al., "Computerized lung sound analysis as diagnostic aid for the detection of abnormal lung sounds: a systematic review and meta-analysis," Respiratory Medicine, vol. 105, Issue 9, pp. 1396-1403 (Sep. 2011).
Jin et al., "New approaches for spectro-temporal feature extraction with applications to respiratory sound classification," Neurocomputing, 123, pp. 362-371 (2014).
Kahya et al., "Classifying respiratory sounds with different feature sets. In Engineering in Medicine and Biology Society," vol. 1, pp. 2856-2859 (Jan. 2006).
Kandaswamy et al., "Neural classification of lung sounds using wavelet coe cients," Computers in Biology and Medicine, 34, pp. 523-537 (2004).
Kelmenson et al., "Prototype Electronic Stethoscope vs. Conventional Stethoscope for Auscultation of Heart Sounds," Journal of Medical Engineering & Technology 38.6, pp. 307-310 (2014). Pub Med. Web.
Kheddache et al., "Acoustic measures of the cry characteristics of healthy newborns and newborns with pathologies," Journal of Biomedical Science and Engineering, 06(08), pp. 796-804 (2013).
Lederman, "Estimation of Infants' Cry Fundamental Frequency using a Modified Sift algorithm," Time, pp. 703-709 (2010).
Miura et al., "Restoration of clipped audio signal using recursive vector projection," Tencon 2011-2011 IEEE Region 10 Conference, pp. 394-397 (Nov. 2011).
Mor et al., "Breath sound distribution images of patients with pneumonia and pleural effusion," Respiratory care, 52 (12), pp. 1753-1760 (Dec. 2007).
Palaniappan et al., "A comparative study of the svm and k-nn machine learning algorithms for the diagnosis of respiratory pathologies using pulmonary acoustic signals," BMC Bioinformatics, vol. 15 (2014).
Patel et al., "An adaptive noise reduction stethoscope for auscultation in high noise environments," J Acoust Soc Am, vol. 103, pp. 2483-2491 (May 1998).
Pesquet et al., "Time-invariant orthonormal wavelet representations," IEEE Transactions on Signal Processing, 44(8), pp. 1964-1970 (1996).

(56) References Cited

OTHER PUBLICATIONS

Reichert et al., "Analysis of respiratory sounds: state of the art clinical medicine," Circulatory, Respiratory and Pulmonary Medicine, 2, pp. 45-58 (Jan. 2008).
Riella et al., "Method for automatic detection of wheezing in lung sounds," Braz J Med Biol Res, 42(7), pp. 674-684 (Jul. 2009).
Sovijarvi et al., "Standardization of computerized respiratory sound analysis," European Respiratory Review, 10(77), pp. 585 (2000).
Taplidou et al., "On applying continuous wavelet transform in wheeze analysis," Conference Proceedings of the International Conference of IEEE Engineering in Medicine and Biology Society, 5, pp. 3832-3835 (2004).
Waitman et al., "Representation and classification of breath sounds recorded in an intensive care setting using neural networks," Journal of Clinical Monitoring and Computing, 16(2), pp. 95-105 (2000).
Website document: "Pocket book of hospital care for children: guidelines for the management of common illnesses with limited resources @online," W. H. Organization, (Jul. 2006). Retrieved:<http://www.who.int/maternal child adolescent/documents/9241546700/en/>.
Website document: the Perch (pneumonia etiology research for child health) project, (1999). Retrieved: <www.jhsph.edu/research/centers-andinstitutes/ivac/projects/perch/>.
Zeskind et al., "Development of translational methods in spectral analysis of human infant crying and rat pup ultrasonic vocalizations for early neurobehavioral assessment," Frontiers in psychiatry, 2(Oct.):56, Jan. 2011.
Zun et al., "The effect of noise in the emergency department," Acad Emergency Med, 12(7), pp. 663-666 (2005).

\* cited by examiner

PROGRAMMABLE ELECTRONIC STETHOSCOPE DEVICES, ALGORITHMS, SYSTEMS, AND METHODS

This application is a U.S. National Stage Application under 35 U.S.C. § 371 of PCT/US2016/059752, filed on Oct. 31, 2016, the entire content of which is hereby incorporated by reference, and claims the benefit of U.S. Provisional Application No. 62/249,028, filed on Oct. 30, 2015, the entire content of which is hereby incorporated by reference.

STATEMENT OF GOVERNMENT SUPPORT

This invention was made with government support under AG036424 awarded by the National Institutes of Health, IIS084611 awarded by the National Science Foundation, N00014-10-1-0278 and N00014-12-1-0740 awarded by the United States Navy Office of Naval Research. The government has certain rights in the invention.

BACKGROUND

1. Technical Field

The currently claimed embodiments of this invention relate to electronic stethoscopes, and more particularly to electronic stethoscopes that provide noise removal and automated classification of auscultation signals.

2. Discussion of Related Art

Despite the many capabilities of modern electronic stethoscopes such as signal amplification, filtering or the ability to record data with secondary applications, they still require extensive training of health care providers for proper content interpretation. Available stethoscopes mainly handle low-level or stationary-like noise, and prove inefficient when it comes to challenging clinical settings with frequent natural, abrupt, non-uniform ambient noise or natural-sound contaminations that limit the clinical value of the chest sounds.

The wide work reported in the literature on computerized lung sound analysis mainly focuses on adult patient populations or controlled-breath auscultation, typically performed in soundproof or well-controlled examination rooms (in an effort to limit undesirable distortions). Most of the work suffers from low adaptability in non-ideal clinical settings.

When auscultation is performed in remote areas or low-resource communities, the clinical setting typically involves rudimentary and noisy environments. In such settings, available health-care providers usually have minimal training, resulting in high inter-observer variability in interpreting findings and high rates of overtreatment or misdiagnosis. In addition, high ambient noise contaminates the lung sound signal and further affects diagnostic capability and accuracy. Examples of contaminating sounds are patient-specific distortions (e.g., crying or motion-originating friction noises) or environmental sounds (e.g., crying in the waiting area, ambient chatter, phones ringing, nearby vehicles passing). Similarly, when auscultation needs to be performed in mobile clinics (an ambulance or helicopter, or the like), or even in a spacecraft, suppressing ambient natural sounds is of paramount importance both for the physicians and any subsequent computerized analysis. Finally, when new physicians are being trained using digitally acquired lung sounds, these need to be noise free to avoid misinterpretation.

There thus remains a need for improved programmable electronic stethoscopes.

SUMMARY

A digital electronic stethoscope according to an embodiment of the current invention includes an acoustic sensor assembly that includes a body sensor portion and an ambient sensor portion, the body sensor portion being configured to make acoustically coupled contact with a subject while the ambient sensor portion is configured to face away from the body sensor portion so as to capture environmental noise proximate the body sensor portion; a signal processor and data storage system configured to communicate with the acoustic sensor assembly so as to receive detection signals therefrom, the detection signals including an auscultation signal comprising body target sound and a noise signal; and an output device configured to communicate with the signal processor and data storage system to provide at least one of an output signal or information derived from the output signal. The signal processor and data storage system includes a noise reduction system that removes both stationary noise and non-stationary noise from the detection signal to provide a clean auscultation signal substantially free of distortions. The signal processor and data storage system further includes an auscultation sound classification system configured to receive the clean auscultation signal and provide a classification thereof as at least one of a normal breath sound or an abnormal breath sound.

A method of processing signals detected by a digital electronic stethoscope according to an embodiment of the current invention includes obtaining an auscultation signal from the electronic stethoscope, the auscultation signal including a target body sound; obtaining a noise signal that includes noise from an environment of the body; obtaining a processed signal by reducing unwanted noise in the auscultation signal based on at least one of the auscultation signal and the noise signal; performing acoustic analysis of the processed signal; and performing statistical analysis of the processed signal.

A computer-readable medium according to an embodiment of the current invention includes non-transitory computer-executable code for processing signals detected by a digital electronic stethoscope, which when executed by a computer causes the computer to obtain an auscultation signal from the electronic stethoscope, the auscultation signal including a target body sound; obtain a noise signal that includes noise from an environment of the body; obtain a processed signal by reducing unwanted noise in the auscultation signal based on at least one of the auscultation signal and the noise signal; performing acoustic analysis of the processed signal; and performing statistical analysis of said processed signal.

BRIEF DESCRIPTION OF THE DRAWINGS

Further objectives and advantages will become apparent from a consideration of the description, drawings, and examples.

DETAILED DESCRIPTION

Figure 1:
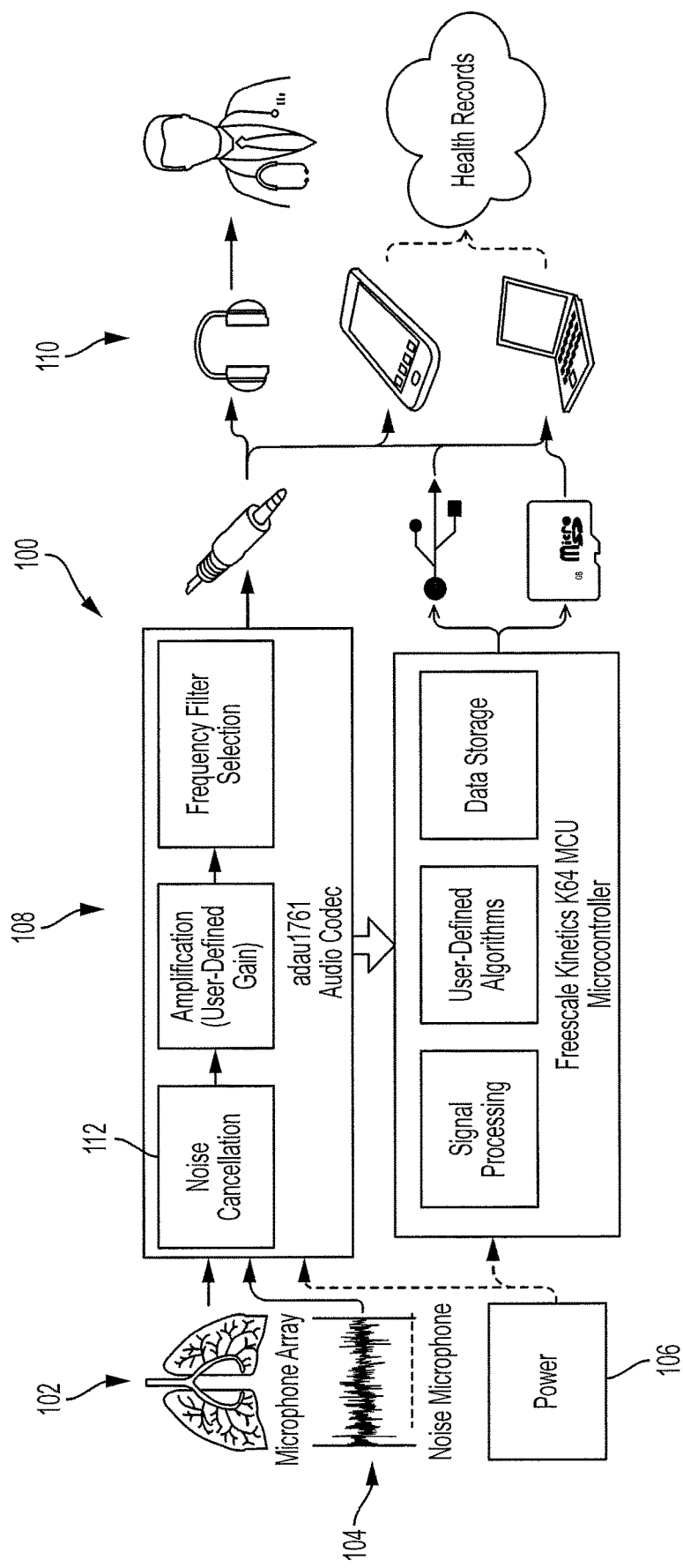
FIG. 1 is a schematic illustration of an electronic stethoscope according to an embodiment of the current invention.

Some embodiments of the current invention are discussed in detail below. In describing embodiments, specific terminology is employed for the sake of clarity. However, the invention is not intended to be limited to the specific terminology so selected. A person skilled in the relevant art will recognize that other equivalent components can be employed and other methods developed without departing from the broad concepts of the current invention. All references cited anywhere in this specification, including the Background and Detailed Description sections, are incorporated by reference as if each had been individually incorporated.

The term "noise" is intended to have a broad meaning to include any types of sounds that interfere with the sounds of interest. Sounds of interest according to some embodiments of this invention include breathing sounds and/or sounds resulting from breathing. In particular, sounds of interest according to this embodiment of the invention can include sounds emanating from a subjects lungs and/or airways. Accordingly, "noise" can include, but is not limited to, stochastic noise other sounds within the subject such as, but not limited to, heartbeats, crying, etc. external sounds such as, but not limited to, other people crying, passing cars, and/or interactions between the use of the stethoscope and the patient such as, but not limited to, scratching sounds of the stethoscope against the subject or the subjects clothing.

According to some embodiments of the current invention, a programmable, electronic stethoscope, as well as systems, algorithms and methods for detecting and processing auscultation signals, offer hardware/software solutions for improved digital auscultation in non-ideal settings and follow-up clinical aid. Some embodiments of the invention can provide a stethoscope that is a smart device, robust in natural ambient noise, that can aid health-care providers deliver an improved clinical diagnosis especially in challenging auscultation environments and remote settings. The smart stethoscope offers a direct solution to the problems of the existing stethoscopes and current studies described above, while also providing the flexibility to implement solutions to future problems. It allows active filtering of ambient noise, using knowledge of the normal and abnormal lung sound profiles to dynamically adapt to abrupt, highly non-stationary environmental noise. While cancelling undesired noise, the technology carefully maintains body sounds that should not be filtered out such as abnormal breathing patterns from the lung which are crucial for diagnosis. The stethoscope can offer an additive array of five sensors for localized lung auscultation. An external microphone captures the concurrent ambient noise and the built-in spectral subtraction implementation suppresses sounds that are unrelated to chest sounds. The algorithm dynamically adapts to the level and profile of the ambient noise and delivers a noise-free signal.

In an embodiment, the stethoscope can allow a user to choose between a digital mode in which the user hears the sounds as digitized and an "acoustic mode". The acoustic mode is designed to sound more similar to conventional, non-electronic stethoscopes since many medical personnel are more familiar with sounds from those stethoscopes. In the acoustic mode, filtering is introduced that makes the electronic system sound like a mechanical unit. To achieve this, the signal is contaminated by the mechanical system and the frequency characteristics are limited. The filter can be engaged by the user activating a switch to toggle between the "true" unfiltered signal and the limited signal from the mechanical system.

The outputted signal can be further processed for removal of subject-specific contaminations including crying and friction noises, and heart sound removal (which is considered noise in the context of lung auscultation), for example. The identified heart sounds can be used for an automated heart-rate extraction. Some embodiments of the current invention can extract further biometric measurements.

Novel feature extraction and machine learning algorithms are then used for an automated detection of abnormal sounds according to an embodiment of the current invention, providing an aid-tool towards objective interpretation of the lung sounds and telemedicine.

Some embodiments of this invention can bridge the gap between true need and commercial availability for programmable electronic stethoscopes. Being highly adaptable to unknown clinical settings, some embodiments of this invention can address the above limitations; and subsequent analysis can provide diagnostic aid to health care providers including patient diagnosing and monitoring, and can increase accessibility to healthcare.

There are many novel parts in this smart device. The use of an array of five electret microphones to achieve uniform spatial sensitivity, which are summed and amplified to record the auscultation signals, rather than the standard stethoscope diaphragm, transducer, or piezoelectric material, not only can reduce cost, but also can provide new and useful capabilities for this electronic stethoscope. Furthermore, an additional external facing microphone to capture ambient noise can be used to provide new and useful capabilities.

Some embodiments of the current invention can provide noise-cancellation and automated diagnosis algorithms, plus the ability to program new algorithms into the stethoscope to provide new and useful capabilities including tailoring for specific patient parameters. The noise suppression scheme according to an embodiment of the current invention is based on a general framework of spectral subtraction algorithms that were adapted to the problem at hand, considering the peculiarities of the lung sound and those of the natural ambient sounds. The signal picked up by the stethoscope's internal microphone (sensor) is assumed to be additive, comprising of the clean (unknown) lung sounds and the concurrent ambient noise. An external microphone further picks up the ambient noise. We augment the general spectral subtraction scheme by first processing the signal into multiple localized frequency bands. Every frequency band is processed individually by different subtraction rules that account for the non-uniform spectral profiles of the ambient noise and natural sounds and their overlapping profiles with the lung sounds. We further alter the general framework by applying distinct subtraction rules per time frame and frequency band; every rule takes into account the current, localized Signal to Noise Ratio, providing high adaptability to sudden unexpected noises from which other Adaptive Noise Cancelling techniques are known to suffer. Finally, during reconstruction we smooth the output result across adjacent signal frames suppressing reconstruction distortions or musical noise typically occurring in spectral subtraction algorithms [1].

The recovered signal is further processed for quality improvement to tackle remaining patient-centric contaminations. We developed methods to address friction noise produced when the stethoscope abruptly comes in contact with the skin, or when it is suddenly displaced. We further developed novel crying identification algorithms to remove recorded intervals that were highly distorted from a subject's crying. Noise suppression schemes on patient-centric contaminations are applied on the single-channel signals.

A heart rate elimination and extraction (HR) algorithm is further implemented using the lung sound signal itself. Automating the extraction of biometric information can be crucial, especially in poor communities, due to lack of personnel; or in pediatric auscultation where minimizing the duration of the visit is paramount, as increased child agitation highly impedes the physician's work. These features will also be useful for general use where patients measure their own response while at home or work. The heart rate extraction and elimination algorithm can provide valuable biometric information while suppressing the heart sounds-irrelevant to the lung sounds of interest.

FIG. 1 provides a schematic illustration of a digital electronic stethoscope 100 according to an embodiment of the current invention. The digital electronic stethoscope 100 includes an acoustic sensor assembly 102 that includes a body sensor portion 104 and an ambient sensor portion 106. The body sensor portion 104 is configured to make acoustically coupled contact with a subject while the ambient sensor portion 106 is configured to face away from the body sensor portion so as to capture environmental noise in the vicinity of the body sensor portion 106. The term "face away" does not require any particular direction and the term "in the vicinity of" does not require any particular distance as long as the "noise" external from the subject that interferes with body sounds can be captured more strongly than body sounds.

The digital electronic stethoscope 100 also includes a signal processor and data storage system 108 configured to communicate with the acoustic sensor assembly 102 so as to receive detection signals therefrom. The detection signals include an auscultation signal including a body target sound and a noise signal. Both signals are digitized for automatic evaluation. The digital electronic stethoscope 100 also includes an output device 110 configured to communicate with the signal processor and data storage system 108 to provide at least one of an output signal or information derived from the output signal.

The signal processor and data storage system 108 includes a noise reduction system 112 that removes both stationary noise and non-stationary noise from the detection signal to provide a clean auscultation signal substantially free of distortions. The noise reduction system 112 can also be referred to as a noise cancellation system. This is not intended to require complete cancellation and can thus be synonymous with noise reduction.

Figure 2:
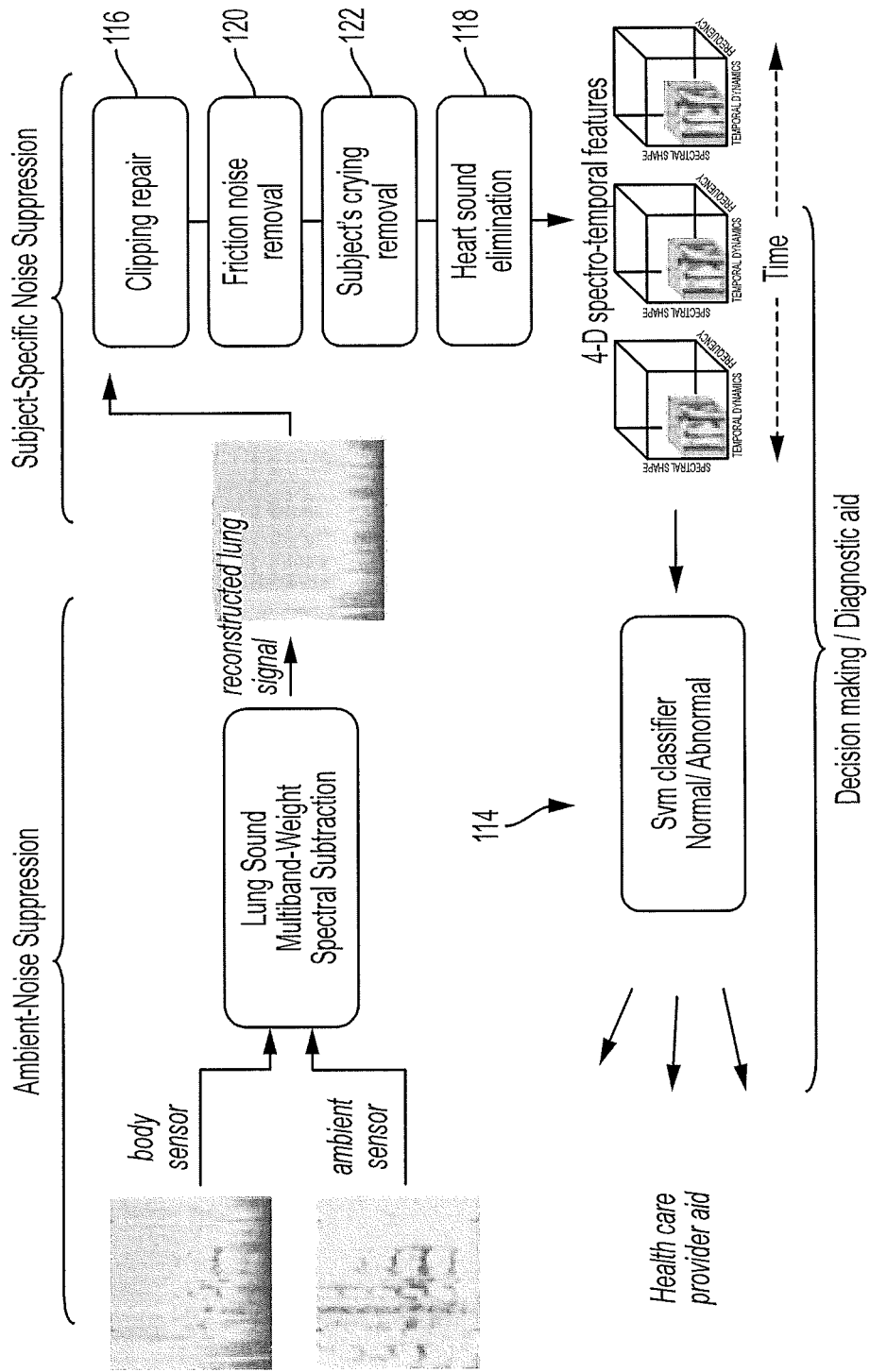
FIG. 2 is a schematic illustration of noise suppression schemes and decision making according to an embodiment of the current invention.

As can be seen more clearly in FIG. 2, the signal processor and data storage system 108 further includes an auscultation sound classification system 114 configured to receive the clean auscultation signal and provide a classification of it into at least one of a normal breath sound or an abnormal breath sound. The classification system is not limited to only binary, e.g., normal vs. abnormal, classifications and can be generalized for further classifications according to some embodiments of the current invention.

In some embodiments, body sensor portion 104 of the acoustic sensor assembly 102 includes a microphone array of a plurality of microphones. In the present case the signals from the microphones are added, however, in other cases the microphone array may be processed to obtain special characteristics such as focusing, e.g., operated in a phased array. The general concepts of the current invention are not limited to a specific number of microphones in the microphone array. In some applications, an array of five microphones has been found to be effective. In some embodiments, without limitation, the microphones can be electret microphones, for example.

In some embodiments, the output device 110 can be at least one of earphones, a smart phone, a personal data assist, or a computer, for example. However, the output device 110 is not limited to only these examples. For example, output could also be stored on-board in some embodiments and the digital electronic stethoscope can be, but is not limited to, a wearable digital electronic stethoscope. Furthermore, the signal processing and/or further processing such as for the decision processes could all be done on-board or with any combination of on-board and external components. For example, the digital electronic stethoscope could be designed to be worm 24/7 for extended periods of time in some embodiments. Also, connections with external devices can be hard wired and/or wireless in some embodiments.

The noise reduction system 112 includes a clipping repair system 116 to repair clipping of the auscultation signal to provide the clean auscultation signal substantially free of distortions. The noise reduction system 112 also includes a heart sound elimination system 118 to remove the subject's heart sounds from the detection signal to provide the clean auscultation signal substantially free of distortions. The noise reduction system 112 can further include a friction noise removal system 120 to remove friction noise of the acoustic sensor assembly rubbing against the subject from the detection signal to provide the clean auscultation signal substantially free of distortions.

The noise reduction system 112 can also include a subject's crying removal system 122 to remove the crying noise of the subject from the detection signal to provide the clean auscultation signal substantially free of distortions.

Further aspects of the current invention will be described below with reference to particular examples. The examples are not intended to limit the broad concepts of the current invention.

Example Hardware Design

The digital hardware design according to an example includes two subsystems—an audio codec and a microprocessor (FIG. 1). The implemented audio codec is the Analog Devices ADAU1761, a low power, 96 kHz, 24-Bit audio codec. Using their SigmaDSP technology and SigmaStudio GUI interface, the added signal from the array of five microphones and the noise signal from the external microphone are used for the real-time noise-cancelation, frequency filtering, and acoustic stethoscope modeling through built-in functions such as band-pass filters and subtraction methods (see below). This codec has an analog output to a 3.5 mm headphone jack and a serial data output interfacing with the microprocessor.

The microprocessor fulfills the many of the other requirements for a 'smart' device implemented by the low-power Freescale Kinetis MK64 microcontroller unit with a USB interface. Currently, the microprocessor is used to control the audio codec and notification LEDs and store audio data on a microSD card. It is also programmed with user-defined algorithms such as heart rate extraction, patient-centric contamination suppression and automated detection of abnormal pulmonary events.

Example Software Design (FIG. 2)

The real-time noise-cancellation is based on spectral subtraction frameworks. Let d(n) be the external microphone recording, x(n) the clean lung sound signal (unknown, desired) and y(n) the recorded signal. Assuming additive sound effects and working within short time frames t, y(n,t)=x(n,t)+d(n,t). In an equivalent frequency (Fourier) representation the phase spectrum of d(n,t) is replaced by the phase of y(n,t) under reasonable assumptions. Since natural sound contaminations are uncorrelated with the signal of interest, we reconstruct x(n,t) via its power spectrum:

$$|X(\omega_k,t)|^2 = |Y(\omega_k,t)|^2 - a_{k,t}b_k|D(\omega_k,t)|^2$$

where k designates differentiation of the reconstruction process within frequency bands; and a,b are special weighting factors dynamically adapted by the current sub-band Signal-to-Noise-Ratio and the spectral characteristics of the lung signals. The algorithmic effectiveness and robustness was evaluated using real pediatric data collected on the field by collaborating doctors. Formal listening tests performed by seventeen enrolled pediatric pulmonologists revealed a 95.1% preference on the reconstructed signals. Compared Adaptive-Noise-Cancelling schemes (FXLMS) proved inefficient in suppressing the external noise interference [1-2].

The reconstructed signal, free of background interferences, is then processed for clipping correction, followed by a friction and patient crying identification algorithm, exploiting fundamental frequency findings during infant crying. Subject-specific noise suppression schemes further identify heart sounds via a Stationary Wavelet Transform, extrapolated and replaced with values recovered from an Auto-Regression predictive model, thus providing a "cleaner" signal with suppressed ambient and body-sound interferences and a Heart-Rate estimation.

A detection algorithm is then applied distinguishing abnormal lung sounds among normal breaths and flagging the existence of potential diseases. A model according to some embodiments of the current invention is based on a multi-resolution analysis extracting 4D spectro-temporal dynamics from the lung sounds (see reference [3] for some background information). This combined feature space has been proven to be more robust than other frequency-based techniques and is complemented by a Support-Vector-Machines classifier. Some results according to an embodiment of the current invention provided 80% accuracy. This can be compared with a 60% accuracy achieved by recent, off-the-shelf conventional approaches, revealing their low-tolerance to more challenging non-ideal auscultation settings.

Some embodiments of the current invention have the potential for significant economic and societal impact in the medical and mobile health fields due to price and usability in multiple environments. Current electronic stethoscopes are very expensive: the 3M Stethoscope can range from USD $339 to USD $396 while the ThinkLabs One Stethoscope sells for USD $499. Their low-adaptability to real challenging scenarios does not justify the high cost and physicians and emergency medical technicians are often discouraged from using them, especially in low-resource clinics. Their built-in noise cancellation fails in challenging clinical environments with natural unexpected sources of noise contaminations. As such, electronic stethoscopes have remained a novelty in the health field. An embodiment of a stethoscope according to the current invention can be manufactured for USD $44, a fraction of the cost of leading electronic stethoscopes. With a lower-cost solution that can be implemented in many different environments and with higher capability, functionality, and customizability, the adoption rate of such devices are expected to greatly increase.

With an increase of electronic stethoscopes and of these devices powered with automated diagnosis, health care becomes accessible beyond established hospitals and clinics. In both the developed and low-resource communities, electronic stethoscopes with robust noise cancelling features and automatic health evaluation capabilities can remarkably increase the ability to provide healthcare through telemedicine, pop-up clinics, and house calls. The societal impact of this device could be substantial, and could far outweigh the economic impact. For chronically ill individuals, the purchase of this inexpensive stethoscope can provide valuable instant feedback to both patient and physician.

Some embodiments of the invention can provide a combination of benefits not provided in existing devices, systems, and methods, including noise cancellation by sophisticated weighted multiband spectral subtraction; analysis algorithms with further single microphone de-noising, biometric measurements (Heart Rate), sophisticated decision making mechanism using spectro-temporal sound extracted features; data storage; and stethoscope sensor using a five-microphone array for localized auscultation and external microphone (ambient noise).

REFERENCES

1. Kelmenson, Daniel A., Janae K. Heath, Stephanie A. Ball, Haytham M. Kaafarani, Elisabeth M. Baker, Daniel D. Yeh, Edward A. Bittner, Matthias Eikermann, and Jaron Lee. "Prototype Electronic Stethoscope vs. Conventional Stethoscope for Auscultation of Heart Sounds." Journal of Medical Engineering & Technology 38.6 (2014): 307-10. Pub Med. Web.
2. S. B. Patel, T. F. Callahan, M. G. Callahan, J. T. Jones, G. P. Graber, K. S. Foster, K. Glifort, and G. R. Wodicka, "An adaptive noise reduction stethoscope for auscultation in high noise environments," J Acoust Soc Am, vol. 103, pp. 2483-91, May 1998.
3. Garrett Nelson, Rajesh Rajamani, Arthur Erdman. "Noise control challenges for auscultation on medical evacuation helicopters." Applied Acoustics, Volume 80, June 2014, Pages 68-78. Web.
4. Emmanouilidou, D.; McCollum, E. D.; Park, D. E.; Elhilali, M., "Adaptive noise suppression of pediatric lung auscultations with real applications to noisy clinical settings in developing countries," Biomedical Engineering, IEEE Transactions on, vol. PP, no. 99, pp. 1,1.
5. Zenk, G. "Stethoscopic detection of lung sounds in high noise environments." Purdue University, West Lafayette.1994.
6. Zun, L., L. Downey. "The effect of noise in the emergency department." Acad Emergency Med, 12 (7) (2005), pp. 663-666.
7. Groom, D. "The effect of background noise on cardiac auscultation," Am Heart J, 52 (5) (1956), pp. 781-790.
8. Arati Gurung, Carolyn G. Scrafford, James M. Tielsch, Orin S. Levine, William Checkley, Computerized lung sound analysis as diagnostic aid for the detection of abnormal lung sounds: A systematic review and meta-analysis, Respiratory Medicine, Volume 105, Issue 9, September 2011, Pages 1396-1403.
9. The PERCH (pneumonia etiology research for child health) project. www.jhsph.edu/research/centers-andinstitutes/ivac/projects/perch/. [19] W.H.O. (2006) Pocket book of
10. D. Emmanouilidou et al., "A multiresolution analysis for detection of abnormal lung sounds," in Engineering in Medicine and Biology Society (EMBC), 2012 Annual International Conference of the IEEE, August 2012, pp. 3139-42.

The following examples describe some embodiments in more detail. The broad concepts of the current invention are not intended to be limited to the particular examples. Further, concepts from each example are not limited to that example, but may be combined with other embodiments of the system.

EXAMPLES

Chest auscultation is a key clinical diagnostic tool for detection of respiratory pathologies. Skilled and highly-trained health care providers are needed to accurately interpret the sound information captured by the acoustic stethoscope and provide a clinical assessment. However, such assessment can be challenged by inter-observer variability during interpretation of chest sounds or by technical restrictions imposed by the stethoscope. In high resource areas, limitations can be addressed by extending the standard of care for pulmonary diseases to include chest radiography, oxygen saturation measurements or even ultrasound; when it comes to resource-poor settings, chest auscultation is typically the only available diagnostic tool, combining low cost and fast diagnosis. In such settings however, skilled physicians are usually unavailable, and environmental noise can highly impede the interpretation of acoustic information. Digital stethoscopes and computerized lung sound analysis come as a natural aid to overcome the imposed limitations. Digital recordings do not suffer from signal attenuation as opposed to acoustic auscultation, and can be further stored and processed offline. Sophisticated signal analysis techniques such as signal enhancement or noise suppression when combined with advanced machine learning algorithms for feature extraction and classification are valuable aid tools for physicians and promise to detect features or patterns that are not easily recognized by human ear.

Pulmonary auscultation aims to capture acoustic signals originating from different sources within the respiratory system, the lung sounds. These sounds consist of multiple components and typically span the range of 50 to 2500 Hz. Breathing airflows of healthy subjects are associated with the term normal lung sounds; additional respiratory sounds when superimposed on normal breaths can be indicative of pulmonary diseases, and are known as adventitious or abnormal sounds. These events of interest can be stationary in nature, like wheeze or stridor; or transient and explosive, like crackles. Although abnormal lung sounds have been extensively studied in the literature, despite their differences, they are not well-defined from a signal processing point of view: for example, wheezes have been reported to span a wide range of frequencies 100-2500 or 400-1600 Hz Similarly, crackles, have been reported within various spectral ranges, below 2000 Hz, or above 500 Hz or between 100-500 Hz with a duration less than 20 msec with energy content in the lower frequency range of 100-500 Hz [21] [24][7].

Acquisition of lung sounds is usually performed by a microphone appropriately attached to the stethoscope. However, the very nature of these acoustic signals, make data acquisition prone to various sources of contaminations, such as ambient, mechanical, environmental or physiological noise, even in controlled clinical settings. These unpredicted noise sources can exhibit interference of varied duration and loudness with a broad range of spectral characteristics that usually overlap with lung sound content [6].

Throughout most of the current published work, auscultation recordings were obtained in a soundproof or quiet room. Noise suppression schemes addressing heart sound reduction have been extensively studied, where linear prediction, adaptive filtering or singular spectrum approaches yielded very promising results. For the majority of these studies, the developed algorithm was applied on a predetermined number of controlled breaths of healthy subjects, with manually extracted inspiration and expiration cycles or where a simultaneous reference signal was available [10] [9]. When it comes to identification or separation of normal from abnormal breaths, the time waveform (temporal information) and the frequency contents (spectral information) have been proven very powerful. Most studies focused on detecting wheeze breaths and crackles: Guntupalli et al [11], Waitman et al [25], Riella et al [22], Mor et al [18], have worked with a Fourier or a Short Time Fourier Transform (STFT) while studies of Kahya et al [13], Kandaswamy et al [14] used the Wavelet Transform for data representation. Sound classification or decision making schemes have been addressed with machine learning approaches such as k-Nearest Neighbor, Neural Networks and Support Vector Machines (SVMs).

This work addresses noise contaminations imposed during auscultation in natural environments. An efficient noise suppression scheme is introduced and the enhanced sounds are then projected to a multidimensional feature space for detecting and classifying abnormal events. The framework is challenged by non-ideal settings during data acquisition, by the young age of the subjects, and by the use of a single recorded signal per patient, without imposing nose clips, simultaneous tracheal or other flow recordings or any kind of controlled breathing on the subjects. Data acquisition details for the recordings used in this example are presented below. The main algorithm in example below starts with a conservative heart sound suppression scheme, followed by a noise elimination algorithm that accounts for stethoscope movement noise and crying contaminations. A multi-resolution analysis is then invoked for feature extraction, capturing temporal and spectral variations of the lung sounds and the final step of statistical analysis is performed by SVM classifiers.

Data Description and Preparation

Data recordings were made available from two studies with different acquisition- and annotation protocols.

Data

Digital auscultation recordings were acquired by the Pneumonia Etiology Research for Child Health (PERCH) study group [4] in busy clinical settings of seven countries including Thailand, Bangladesh and 5 African sites. Children were enrolled to the study with either severe or very severe clinical pneumonia, as defined by the World Health Organization [4a]; or were enrolled as community controls (without clinical pneumonia). In total, 1157 children were enrolled ranging from 1 to 59 months with an average age of 11 (+−11.43) months.

According to the PERCH protocol, 9 body locations were auscultated for 7 s each. The last location corresponded to the cheek position and was not considered in further analysis. Signals were acquired using a digital ThinkLabs Inc. commercial stethoscope sampling at 44.1 KHz. An independent microphone was affixed on the back of the stethoscope, recording concurrent background contaminations and environmental noises that could be corrupting the lung sound signals. During auscultation the child was seated, laid down or held to the most comfortable position and signals were recorded at the child's normal breath.

Annotations

Annotation labels were made available for the full dataset by a panel of 8 reviewers and one expert reader. Every 7 s interval was annotated by two distinct reviewers; each reviewer indicated a "primary" and a "secondary findings" label from the list of available labels in Table I. A label would be registered as "definite" only if the particular finding could be heard within at least two full breath cycles. For example, if a reviewer heard wheezing sounds within a recorded interval, and such a finding were heard during at least two full breaths, then a "definite wheeze" label would be registered for the interval; but if, according to the reviewer, only a single breath contained wheezing sounds, then the interval would be registered as a "probable" wheeze. In the case where an ambiguous sound occurred and the reviewer could not distinguish the particular abnormal/adventitious sound (either due to poor sound quality, or severe crying contamination), then an "interpretable" label would be assigned. In case of disagreement among the reviewers, a $3^{rd}$ or a $4^{th}$ reviewer-arbitrator was used to resolve ambiguities. The expert reader provided a final annotation for the unresolved cases.

TABLE I

PERCH DATASET ANNOTATION LABELS USED IN THE STUDY

| Label | Comments |
|---|---|
| Normal | normal lung sounds |
| Wheeze | wheezing breaths |
| Crackle | presence of crackle |
| Crackle & Wheeze | presence of both crackle and wheeze |
| Uninterpretable | Undetermined adventitious or corrupted sound |

Before continuing, a brief introduction into the peculiarities of the data is necessary. As briefly mentioned above, the busy or outpatient clinic environments make most of the recordings prone to environmental noise contaminations and create inherent difficulties when analyzing signals for both the physicians and the computerized methods. Some typical examples of contaminations include family members chatting and children crying in the waiting room, musical toys ringing nearby, vehicle honks, mobile or other electronic interference, all considered within the challenging scope of pediatric auscultation.

Preprocessing

All acquired recordings were low-pass filtered with an anti-aliasing $4^{th}$ order Butterwoth filter at 4 kHz cutoff; then resampled at 8 kHz and whitened to have zero mean and unit variance. This down-sampling is justified by considering the nature of the recorded signals and the guidelines of the CORSA project of the European Respiratory Society [23] and related published works [23][23]: normal respiratory sounds are typically found between 50-2500 Hz, tracheal sounds can reach energy contents up to 4000 Hz and heart beat sounds can be found in the range of 20-150 Hz. Furthermore, wheeze and crackle, the commonly studied adventitious events, typically have a range of 100-2500 Hz and 100-500 (up to 2000) Hz respectively; other abnormal sounds include stridors, squawks, rhonchi or cough, and exhibit a frequency profile below 4 kHz. Therefore, with regards to the respiratory sounds, no crucial information loss was expected after resampling.

Main Algorithm

Noise Elimination and Heart Sound Suppression

Pediatric auscultation performed in outpatient or busy clinics is susceptible to a combination of noise sources, varying from environmental sounds to child's agitation and crying. Excerpts heavily contaminated with noise are expected to carry no audible lung sound information and further analysis is prompt to merit upon their exclusion. According to [6] such contaminations can corrupt both the time waveform and spectral characteristics of the acoustic sounds.

Smoothing Out Clipping Distortion

Lung sounds are fade signals than can only be captured when the recording microphone is placed in touch with—or very close to—the sound source, i.e. upper and lower thoracic areas. If during the recording process the amplitude of the signal exceeds the allowed amplitude range, as determined by system's specifications, then all exceeding values are truncated with the upper/lower thresholds producing signal distortion known as clipping. While distortion is created in the time domain, it also results in higher frequency harmonics in the frequency domain, where simple filtering techniques might not be enough to overcome the distortion [17] [3].

(i) Clipping Detection. Considering the nature of the lung sound signals, it is highly unlikely to find regions of constant amplitude during normal function of the stethoscope. Therefore, clipped regions were identified as consecutive time samples with constant maximum-value amplitude (up to a small perturbation tolerance of 15%).

(ii) Repairing Clipping Distortion. Cases of high amplitude values such as loud abnormal sounds, subject's crying or talk close to the microphone, have high probability of being clipped. In this context we can claim an a priori knowledge on the state of the signal based on the near past or future, and seek reconstruction with statistical methods. However since the clipping intervals are typically in the order of a couple of samples per region, the complexity of such statistical methods and assumptions were not found necessary here. For the approximation of the clipped values a smooth numeric interpolation method was invoked using piecewise cubic interpolation (splines) given knowledge of a close neighborhood around each identified region.

Ambient Noise Suppression: Multiband Spectral Subtraction

Spectral subtraction algorithms are typically used in fields of communication or speech enhancement for noise reduction; the general scheme assumes a known measured signal y to be comprised of two signal components: an unknown desired signal x and a known or approximated interference signal y=x+n. In this work, x corresponds to the true, clean lung sound signal which we wish to recover, and n corresponds to the noise leakage into the stethoscope recording and will be approximated using the externally mounted microphone on the back of the actual stethoscope. The algorithm operates in the spectral domain in short time windows to account for stationarity assumptions. Further assumptions of no correlation between the desired undistorted lung sound signal and the ambient noise lead to the power spectral density representation $X^2=Y^2-N^2$, where X, Y, N correspond to the short time discrete Fourier Transform of x, y, n respectively. In our previous work [4b] we have extended this basic design and augment the subtraction scheme to account i) for localized frequency treatment by distinctly processing individual frequency bands, in a manner tailored to the spectral characteristics of the desired and the noise signal; ii) for localized time window treatment by considering the local Signal To Noise Ratio (SNR) information and adjusting extra for high SNR time frames; and iii) reconstruction distortions including "wind tunnel" noise effects, by smoothing signal estimates along adjacent time frames and frequency bands. In the resulting lung sound estimate, ambient noise of any kind has been highly suppressed or fully eliminated. See [4b] for a detailed discussion.

Mechanical or Stethoscope Noise (i) Transition between Auscultation Sites. This type of noise usually occurs when the physician changes between auscultation sites or in similar settings when the electronic stethoscope is moved from one body area to another. It comprises of a silent period (or one with negligible amplitude), having amplitude discontinuities at the edges. While such contamination might seem insignificant, confusion is likely to be introduced into subsequent computerized analysis since possible sharp transitions produce irregular energy contents in the spectrum profile. For the identification of the silent regions a simple low-amplitude threshold was used; the identified regions were excluded.

(ii) Abrupt Stethoscope Displacement. Noise produced by such displacements is attributed to intentional quick stethoscope transitions made by the physician; or unintentional sharp displacements as a result of subject's agitation during auscultation. This is a common type of noise especially for infant subjects and is treated separately due to its unique profile. Sharp stethoscope movements like these are typically followed by friction with the body and produce unwanted short-time broadband energy bursts. These regions were identified as follows:

(a) The magnitude of the Short Time Fourier Transform (STFT) or spectrogram was computed using a 10 msec window and 50% overlap and normalized to [0,1]. Since we are looking for broadband events, the region of interest (ROISRTF) was defined to be spectral content above 1 KHz with a frequency span more than 1.5 KHz.

(b) Within the ROISRTF, the average spectral energy of each time frame, $E\tau$, was compared to the total average energy of all ROISRTF, $E\mu$ and frames with $E\tau>2xE\mu$ were considered candidates. A final selection rejected consecutive candidate frames exceeding 100 msec of duration while all remaining candidate frames were deemed Abrupt Stethoscope Displacement noise, and were replaced using a stationarity index and the ARMA model described below.

(iii) Subject's Intense Crying. The multiband spectral subtraction scheme described previously is very efficient for eliminating ambient crying occurrences. However, when the child under auscultation is crying, reverberation effects are prominent all over the chest wall and back body area. As a result, the subtraction algorithm will be able to suppress but not fully eliminate the interference and thus an extra step of crying identification and elimination is needed.

Figure 3:
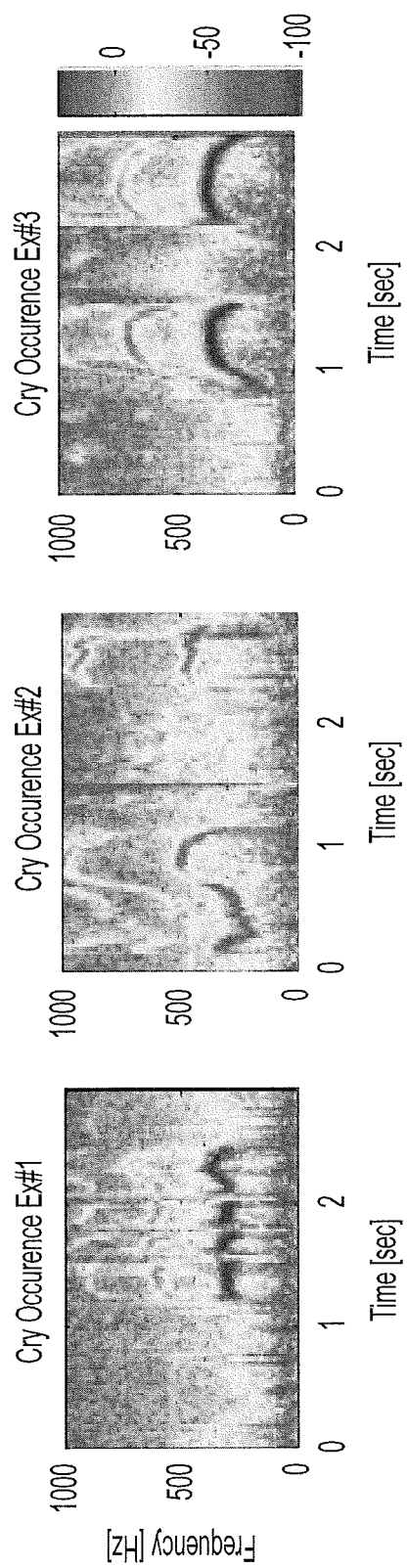
FIG. 3 shows spectrogram examples of crying occurrences. Notice that wheeze sounds can exhibit similar profiles.

Depending on the cause of irritation, infants and young children broadcast crying vocalizations, seen as high-pitch sounds comprising of varying temporal and frequency signatures (see FIG. 3). These sounds can be categorized into the following modes: phonation (or normophonation), consisting of the typical cry with a harmonic structure and a fundamental frequency ranging in 400-600 Hz or 350-750 Hz; hyperphonation mode, also harmonically structured but with rapidly changing resonance and a shifted fundamental frequency of 1000-2000 Hz or even higher. This high-pitched crying is often emitted by children in major distress or important pain, or infants who show biomedical indices of high risk; dysphonation mode, consisting of crying intervals with aperiodic vibrations (i.e. no measurable harmonic structure) occurring mostly as a result of pain or child arousal and can be indicative of poor control of the respiratory system [16] [26] [15]. Identifying dysphonation cry modes are beyond the scope of this example; hyperphonation cases are rarely expected to occur and are briefly addressed in this work, where we primarily focus on phonation cry mode.

Instances of phonation and hyperphonation crying modes can be localized using properties of the time-frequency representation (spectrogram) of the signal. Elevated frequency contents within the ranges of 200-600 Hz or above 1000 Hz, combined with a harmonic structure can be highly indicative of such events. However when these events are considered within lung sound content, caution is needed: adventitious sounds can produce patterns of similar or overlapping specifications as shown in FIG. 3.

With an aim to identify long, loud, fully corrupted crying intervals, short, soft crying or vocalized intervals were decided not to be considered: they might contain concurrent audible adventitious breath sounds and from the physician's point of view, such intervals can be valuable for the final assessment, as opposed to intense crying. A decision was made for every short0time 100 ms frame using pitch estimation and a trained classifier. To avoid confusion with possible adventitious occurrences during inspiration or expiration, a minimum of $T_{dur}$=600 ms was required for crying segments. $T_{dur}$ was set considering respiratory rate standards [12], where subjects in this study expected to have a rate of 18 to 60 breaths per minute. The crying identification process is as follows:

(a) The auditory spectrogram representation (8 ms analysis window) was calculated for every frame as described in (6). A pitch estimate for every window was calculated by spectral filtering via a bank of frequency modulated gaussian/gabor filters. The dominant pitch per window was then extracted and the average pitch (excluding 20% of the distribution tails) constituted the resulting pitch estimation per frame. Frames with an extracted pitch lower than 250 Hz were immediately rejected.

(b) Spectro-temporal dynamics features were extracted from the candidate frames using (6)-(8), and were fed to a pre-trained, binary Support Vector Machines (SVM) classifier. The radial basis functions SVM was used to distinguish crying instances from other perplex voiced adventitious sounds such as wheeze.

The identified regions of intense, long cry were excluded from further analysis.

Eliminating Heart Sound Interference

Heart Sound (HS) provides valuable clinical information for the patient and is usually part of the standard biometric measurements taken in a routine assessment. The heart rate combined with the waveform of the heart beat can be very indicative in case of disease. However in the context of auscultation, it proves to be another noise component masking the respiratory sounds. The problem of HS suppression has been addressed in several studies [8]. Once the HS segments are identified they can be replaced using adaptive filtering or numerical interpolation techniques, acting on the time waveform, the wavelet domain or frequency domain, where the most promising ones seem to be wavelet and STFT techniques. Here we invoke an Auto-Regressive/Moving Average (ARMA) method to fill up the extrapolated intervals, which are identified by a wavelet multi-scale decomposition, inspired by [8].

(i) Heart Sound Identification: Identifying heart beats on heart auscultation can be a tedious task on its own. On lung sound recordings it can be even more challenging since the heart sound waveform is highly "corrupted" by lung sound and inherent noise. Therefore, when it comes to busy clinics and pediatric auscultation we need to relax the goal of high accuracy to low specificity. In other words, we treat this task very conservatively to avoid any false alarms coming from possible adventitious events. With the aim of suppressing the heart sounds in a scenario of no false alarms, we propose the following algorithm.

The original lung sound signal is band-pass filtered in the range of [50, 250] Hz and down-sampled to 1 kHz just for identification purposes. This preprocessing aims to make the heart beat components more prominent by suppressing lung sound and noise components outside this range. Then the Discrete Wavelet Transform (DWT) is obtained at depth=3. The decomposition filters used are obtained from the symlet filter family. Due to its shape, the symlet waveform can be used to capture heart beat irregularities in the signal. Here, instead of DWT we have used the Discrete Static Wavelet Transform (SWT). The only difference is that SWT is time invariant as opposed to DWT: after the Detail and Approximation coefficients, $D_j(n)$ and $A_j(n)$, are obtained, signals do not undergo downsampling. The reconstruction of the original signal can be easily obtained by averaging the inverse wavelet transforms [20].

The resulting wavelet representation is used to identify irregularities corresponding to heart beats. It is well known that as the scale level increases, the signal singularities become more apparent, a property that has been used extensively in image processing. The multiscale product $P_{1:J}(n)$ of the J approximation coefficients is used for the purpose:

$$P_{1:J}(n) = \prod_{j=1}^{J} SWT_j\{x(n)\} \quad (1)$$

where $SWT_j$ is the wavelet decomposition at the j-th scale level and x(n) is the lung sound signal. The components at every scale are normalized before forming the product. We then act on the approximation coefficients $A_j(n)$ and exclude all regions identified by the multiscale product. These excluded intervals correspond to heart sounds that will be replaced by estimated data, as explained below.

(ii) An ARAM model is invoked for the missing data estimation. We consider the lung sound signals as a locally stationary random process (wide-sense). That is, individual short-time intervals of the lung sound signal are expected to be stationary and we are interested in predicting the missing data from past or future values. First a stationarity check was performed on the neighboring area of the removed segment. If the segment following the gap was found not to be stationary, then a forward linear prediction model was used. In the opposite case, a backward linear prediction model was used.

The one-step forward linear predictor is formed as follows:

$$\hat{x}(n) = -\sum_{k=1}^{p} a_p(k)x(n-k) \quad (2)$$

where $\{-a_p(k)\}$ are the prediction coefficients of our order-p predictor. We solve for the coefficients by minimizing the mean-square value of the prediction error $\{x(n)-\hat{x}(n)\}$ which leads to the normal equations involving the autocorrelation function $\gamma_{xx}(l)$:

$$\sum_{k=0}^{p} a_p(k)\gamma_{xx}(l-k) = 0 \quad (3)$$

with lags l=1, 2, . . . , p and coefficient $a_p(0)=1$. The Levinson-Durbin algorithm was invoked to efficiently solve the normal equations for the prediction coefficients.

The one-step backward linear predictor of order p is formed as follows:

$$\hat{x}(n-p) = -\sum_{k=0}^{p-1} b_p(k)x(n-k) \quad (4)$$

Solving for coefficients $\{-b_p(k)\}$ by minimizing the mean square prediction error yields the same set of linear equations as in (3). The order p of the linear prediction models was determined by the length of the particular heart sound gap and a maximum order $p_{max}=1000$, corresponding to about 125 msec.

In order to check the neighboring intervals for stationarity we partitioned each segment into M non-overlapping windows of length L. Then, according to Wiener-Khintchine theorem, the power spectral density (PSD) of the m-th segment, $\Gamma_{xx}^m(l)$, was computed as the Fourier transform of the autocorrelation function and the following spectral variation measure was introduced [1].

$$V(x) = \frac{1}{ML}\sum_{l=0}^{L-1}\sum_{m=0}^{M-1}\left(\Gamma_{xx}^l(k) - \frac{1}{M}\sum_{k=0}^{M-1}\Gamma_{xx}^k(k)\right)^2 \quad (5)$$

A zero value for the above quantity indicated that the segment is a WSS process. For the estimation of the PSD the multitaper periodogram was preferred to the periodogram, as it typically results in smaller variance.

It is important to note that we are aiming for a very conservative approach due to the challenges of the inherent recorded noise and the presence of adventitious events. Intervals identified for exclusion by the multiscale product in (1) were chosen after a high-value threshold; among the remaining regions an amplitude check was further enforced: if the identified region was part of a high-amplitude time-interval as compared to the average signal amplitude, then the heart sound was chosen not to be eliminated. Furthermore, if the peak-to-peak interval for identified heart sounds was too short w.r.t pediatric standards [19], then the corresponding regions were also kept intact.

For non-noisy recordings of normal subjects, such conservative approach might not be needed as discussed in section I; however, in this work these criteria will ensure non-distortion of adventitious intervals and a minimum false positive rate.

Acoustic Analysis

After the noisy intervals have been removed and the heart sounds suppressed, an appropriate representation space is needed to capture data characteristics. As discussed in Section I, temporal or spectral representations have been proven to capture the lung sound signal components adequately. We invoke a multi-resolution approach, one that exploits both the spectral and the temporal dynamic changes of the signal and is based on psychophysical and physiological findings of the auditory pathway in the brain. Such an approach has been shown to provide a sufficient representation space for the analysis of auscultation recordings. We present below the main analysis steps and more details can be found in [5].

A bank of 128 cochlear filters h(t; f), with 24 channels per octave, was used to analyze the sound signals s(t). These filters were modeled as constant-Q asymmetric band-pass filters and tonotopically arranged with their central frequencies logarithmically spaced. Then, signals were preempasised by a temporal derivative and spectrally sharpened using a first-order difference between adjacent frequency channels, followed by half-way rectification and a short-time integration $\mu(t; \tau)$, with $\tau$=8 msec. An enhanced spectrogram y(t,f) is thus obtained, also called the auditory spectrogram [2]:

$$y(t,f) = \max(\partial_f \partial_t s(t) * h(t,f), 0) *_t \mu(t;\tau) \quad (6)$$

Having obtained the auditory spectrogram, signal modulations along both time and frequency axes are then captured through a multiscale mechanism, as inspired by processes of the central auditory stage. Along the logarithmic frequency axis, y(t,f) is passed through a bank of symmetric filters formed by the seed function $h_S(f)$ and it's dilations $h_S(f;\Omega_c)$ with modulation frequency $\Omega_c$ measured in cycles/octave (c/o). In more details, $h_S(f)$ is the second derivative of a Gaussian pdf with zero mean and variance $2/\pi^2$, having the following normalized Fourier Transform:

$$H_s(\Omega; \Omega_c) = H_s\left(\frac{\Omega}{\Omega_c}\right), \text{ with} \quad (7)$$

$$H_s(\Omega) = \Omega^2 \exp(1 - \Omega^2)$$

Notice that having 24 channels per octave, the maximum spectral resolution (scale) is 12 c/o. Here 28 such filters were used, with scaling value in $2^{[-5:0.3:3,3]}$ c/o. Along the time axis, asymmetric filters were used of the form $$h_g(x) = \Omega_c \cos(2\pi t) t^3 \exp(-\beta t) \quad (8)$$

The time slices of the auditory spectrogram were filtered in using the Fourier representation of (8), $H_R(\Omega)$ as a seed function for different modulation rates $\Omega$, measured in Hz. A bank of 21 filters was constructed by dilating the seed function and creating filters of the form $H(\Omega/\Omega_c)$ to capture fast and slow temporal variations for modulations $\Omega_c$ in $2^{[0.1:0.3:6.2]}$ Hz and $\beta$=4. Making use of positive and negative signs for the rate parameter, these filters can also capture directionality of the changes, ex a positive rate corresponds to downward moving energy contents and a negative rate corresponds to upward moving energy contents.

Statistical Analysis and Decision Making

The high dimensionality of the feature space presented above can be proven an obstacle for further analysis. Thus, tensor Singular Value Decomposition (SVD) was used for the purpose. Data were unfolded along each feature dimension and the principal components were calculated from the covariance matrix. By keeping components capturing no less than 99% of the total variance, the dimensionality was highly reduced from 28×42×128 to at most 6×8×11.

For classification purposes supervised learning with binary SVMs and radial-basis kernels (RBF) were used. The technique of RBFs allows data mapping from the original space onto a new linearly separable representational space. In the 2-class problem encountered here, data were grouped into normal versus abnormal breath sounds. Data in the normal group came from control subjects (with possible upper respiratory disease), while the abnormal group was formed by intervals that have been annotated as containing either wheeze or crackles, or both. Segments for both groups were randomly chosen from a large pool of available data, and it is possible that segments are corrupted by noise or other technical difficulties. For training (testing) purposes 90% (10%) of the data were kept. Naturally the SVD space was built using only the training data and dimensionality of the testing data was reduced by projection. To further account for performance bias, 50 Monte Carlo runs were used.

Comparison with Other Studies

Here we investigate the feature space of the current study and its ability to properly capture adventitious lung sound events by comparing it with state of the art feature extraction methods of previously published literature. Palaniappan et al. in [27] demonstrate the effectiveness of the Mel-frequency cepstral coefficients (MFCCs) for capturing the spectral characteristics of normal and pathological respiratory sounds. They are powerful features, widely used in audio signal processing, and especially in speech recognition or speaker identification systems. MFCCs are a type of nonlinear cepstral representation and are calculated on a mel scale frequency axis, one that approximates better the human auditory system's response [28]. First, the logarithm of the Fourier transform is calculated, using the mel scale, and then its cosine transform. The resulting spectrums provide one coefficient per frequency band and constitute the MFCCs amplitudes. For the purposes of this study we call this method MFCC_P. and according to [27], 13 MFCCs were extracted; a window length of 50 ms was used with 25% overlap.

In a different study by Jing et al [29], a new set of discriminating features was proposed for extracting normal and adventitious sounds even from low respiratory sounds, based on spectral and temporal signal characteristics. The features were extracted from a refined spectro-temporal representation, the Gabor time-frequency (Gabor TF) distribution. Each resulting frequency band is used for the extraction of multiple features: a mean instantaneous kyrtosis calculation is used as a feature for adventitious sound localization; a discriminating function produces signal predictability features, and a sample energy histogram distortion calculation is further used as a nonlinear separability criterion for discriminating between normal and abnormal breath sounds. As the order of the Gabor TF representation increases, it converges to a Wigner-Ville distribution and the latter is used to extract the features in [29]; such method will be called WIGNER_J herein.

PERCH database was used for the comparison among methods MFCC_P, WIGNER_J and the proposed method, PROPOSED. For comparison purposes we only considered intervals with a "definite" label for which the two reviewers were in agreement. Group Abnormal contained lung sound intervals whose primary label indicated the existence of Crackles, Wheeze or Crackles and Wheeze and for which the two reviewers were in agreement. Group Normal contained recorded intervals that had a "Normal" primary label and for which reviewers were in agreement, excluding segments with an abnormal (Crackle/Wheeze) secondary annotation. Each 10 s annotation was split into 3 s segments, with 75% overlap. Notice here that a 10 s segment annotated with an adventitious event, if split into sub-intervals of 3 s, then only a subset of them will be truly abnormal sounds, while the rest of them will contain no occurrence of adventitious sounds. Furthermore, while a normal annotation rules out wheeze or crackle occurrences, the lack of other abnormal breaths such as upper respiratory sounds is not ensured.

All feature extraction methods were complimented by a binary SVM classification with RBF kernels. For the calculation of specificity and sensitivity, 50 Monte Carlo repetitions were used on a 10-fold cross validation. During cross validation, the subjects included in the training and testing sets were mutually exclusive, to avoid classification bias.

Comparative results are shown in Table II, revealing the superiority of the current feature extraction method. Sensitivity and specificity indices correspond to the number of correctly identified abnormal and normal breath sounds, respectively. Accuracy index depicts the average of Sensitivity and Specificity indices. Low accuracy percentages of the WIGNER_J method are noticeable. It is an expected outcome considering the nature of the extracted features: they are designed to detect unexpected abnormal patterns (thus the high Sensitivity value) but the feature space lacks the ability of separating respiratory-related abnormal sounds from noise-related sounds or signal corruption, and so, without further improvement, this method is not suitable for real-life auscultation scenarios. The superiority and the noise robustness of the proposed feature space are revealed: the algorithm is equally good at identifying both abnormal and normal breath sounds with no bias towards one of the groups.

TABLE II

COMPARISON OF FEATURE EXTRACTION METHODS: CLASSIFICATION RESULTS

|  | Sensitivity % | Specificity % | Accuracy % |
|---|---|---|---|
| MFCC_P | 68.98 | 72.89 | 70.94 |
| WIGNER_J | 77.81 | 43.59 | 60.70 |
| PROPOSED | 81.66 | 79.50 | 80.58 |

*Results are computed on individual 3 s segments

Results
Noise Elimination and Heart Sound Suppression

Figure 4:
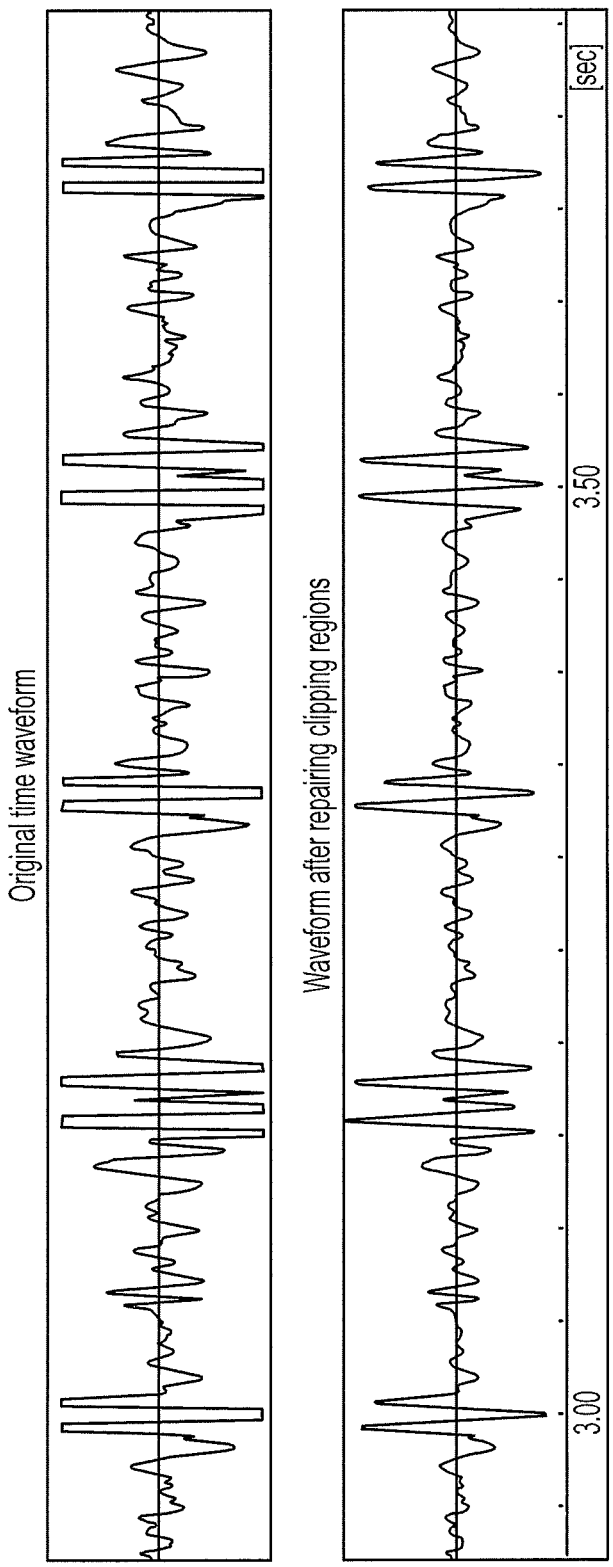
FIG. 4 provides an example demonstrating clipping restoration according to an embodiment of the current invention. Notice how the distorted regions of the original waveform are restored and smoothed out.

The clipping regions for all signals were identified and repaired according to the described algorithm. A visual inspection of the processed signals revealed no artifacts. The outputted waveforms kept the characteristics of the original time signal with the benefit of repaired clipping distortions, as shown in FIG. 4.

The next step was identification and elimination of the intervals highly contaminated with stethoscope movement noise and intense crying. Noise produced by subject's crying or short-time stethoscope displacements was replaced by silent segments.

Figure 5:
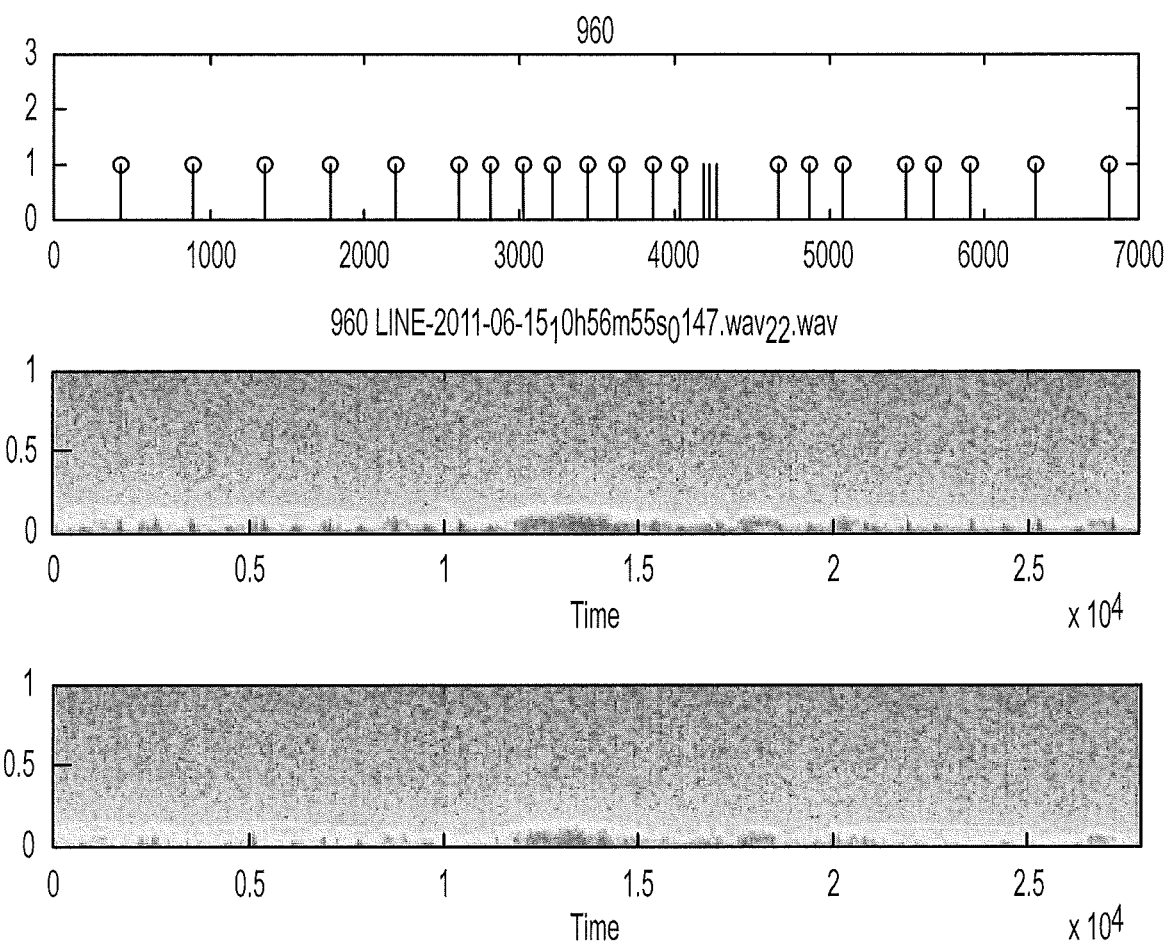
FIG. 5 shows an example for heart sound identification and suppression according to an embodiment of the current invention.
Figure 6A:
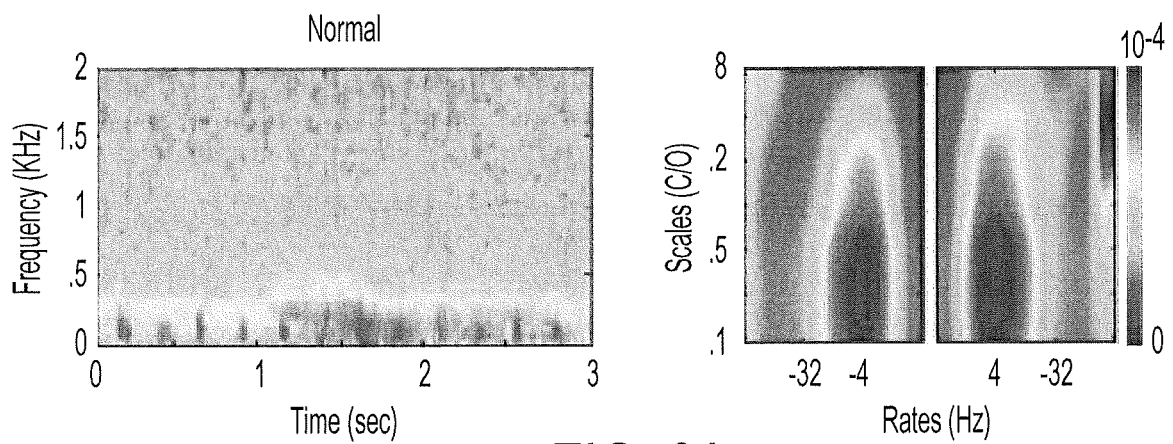
FIG. 6A-6C show example spectrogram (left) and rate-scale (right) representations of a normal (a), crackle (b) and wheeze (c) segment. Notice the crying occurrence corrupting (b) at 2.5 s and how the spectrogram representation is inadequate to distinguish it from a wheeze case, whereas in the rate-scale profile (right) such a distinction is clear: the crackle case exhibits a broadband energy profile while the wheeze case a strongly asymmetric one.
Figure 6B:
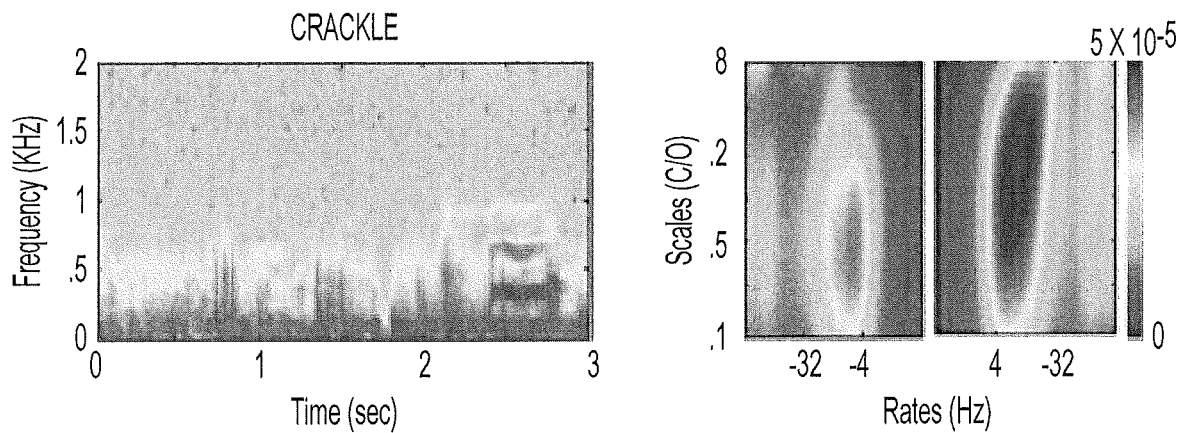
Figure 6C:
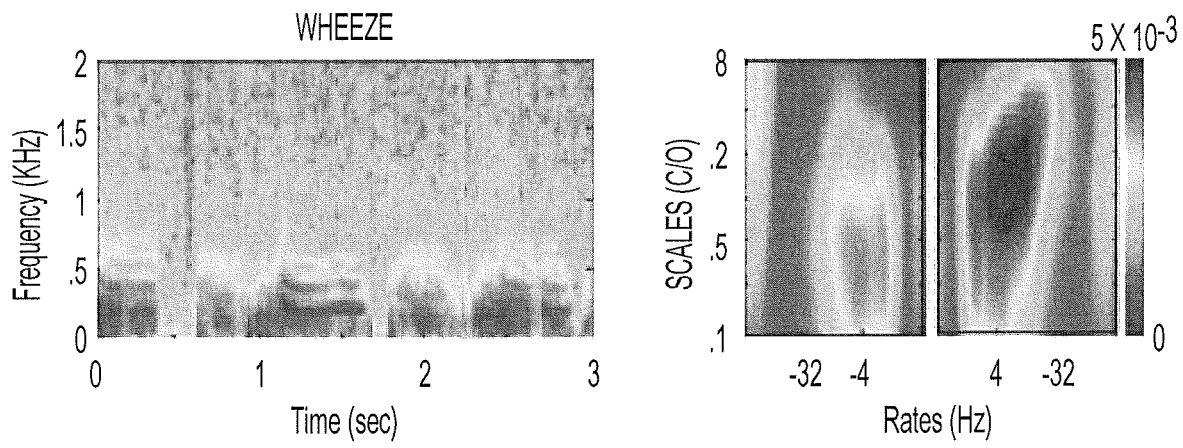

Heart sound identification is illustrated in FIG. 5 (top). The vertical lines correspond to indicators of heart sound candidates. After rejecting regions achieving low multiscale product using (1), the algorithm keeps only the round dot indicators. The spectrogram of the input signal and the output after heart sound suppression in the identified regions is shown middle and lower portions of FIG. 5.

An important aspect which has not been addressed yet is the length of the data. After data preprocessing, application of the heart sound reduction, noise elimination algorithms, and before feature extraction we face the need of a suitable window length to partition the long recorded signals. The question is how long or short of a window should we use and why. A very short window will tend to enhance signal irregularities and result in great heterogeneity among training data, especially under noisy conditions. Noise interferences apparent in both normal and abnormal breaths that have similar or overlapping short-time signatures with adventitious events can introduce high confusion to the classification/decision scheme. On the other hand, distinct features of short adventitious events might tend to fade away when using a long window. On this aspect we considered an overview analysis while using various windows sizes to process the data.

We note here the possibility of adventitious event occurring in the control group. However if those intervals were not found alarming by the physician, the corresponding subject becomes part of the control group. When a fixed window of length $L_N=3$ s is chosen, caution is needed when forming the data. Signals were segmented into 10 s intervals in accordance to the available annotations. Segments coming from the control group, labeled as normal by both reviewers (having no crackle or wheeze breaths as primary or secondary findings) were randomly chosen as part of the normal group. Similarly, 10-sec segments coming from either the control or the non-control group, annotated for crackles and/or wheeze by both reviewers (in primary or in secondary findings) were randomly chosen to form the abnormal group. Both "definite" and "probable" annotations were included. All intervals were then split into 3 s excerpts by keeping the original site location annotation.

Performance evaluation is not a trivial task in such a setup: the classifier produces a decision for every sub-interval, while a decision per site location (10 s segments) is desired. We employ a simple rule while taking into consideration the expected duration of the adventitious events. Within a site location, if at least M consecutive sub-intervals were determined to be abnormal after the classifier. Considering the overlap percentage, M was chosen to be equal to 5. To illustrate this process, consider all overlapping 3 s subintervals constituting a 10 s annotation. If at least M=5 consecutive sub-intervals were classified into the abnormal group, then the particular 10 s interval was assigned an abnormal label; otherwise the interval was assigned a normal label. Evaluation results are shown below in Table III.

TABLE III

FINAL CLASSIFICATION RESULTS PER SITE LOCATION

|  | Sensitivity % | Specificity % | Accuracy % |
|---|---|---|---|
| PROPOSED | 72.41 | 80.85 | 77.13 |

*Performance is evaluated per site location (10 s decision)

REFERENCES FOR EXAMPLES SECTION

[1] Prabahan Basu, Daniel Rudoy, and Patrick J Wolfe. A nonparametric test for stationarity based on local Fourier analysis. *Acoustics, Speech and Signal*, pages 3005-3008, 2009.

[2] T. Chi, P. Ru, and S. Shamma. Multiresolution spectrotemporal analysis of complex sounds. *J. Acoust. Soc. Am.*, 118:887-906, 2005.

[3] Abdelhakim Dahimene, Mohamed Noureddine, and Aarab Azrar. A Simple Algorithm for the Restoration of Clipped Speech Signal. *Informatica*, 32:183-188, 2008.

[4] (1999) The PERCH (pneumonia etiology research for child health) project. www.jhsph.edu/researchkenters-andinstitutes/ivac/projects/perch/.

[4a] W. H. Organization, "Pocket book of hospital care for children: guidelines for the management of common illnesses with limited resources @online," july 2006. [Online]. Available: http://www.who.int/maternal child adolescent/documents/9241546700/en/

[4b] Emmanouilidou, D.; McCollum, E. D.; Park, D. E.; Elhilali, M., "Adaptive noise suppression of pediatric lung auscultations with real applications to noisy clinical settings in developing countries," Biomedical Engineering, IEEE Transactions on, vol. PP, no. 99, pp. 1,1

[5] D. Emmanouilidou, K. Patil, J. West, and M. Elhilali. A multiresolution analysis for detection of abnormal lung sounds. In *Engineering in Medicine and Biology Society (EMBC), 2012 Annual International Conference of the IEEE*, pages 3139-3142, August 2012.

[6] Dimitra Emmanouilidou and Mounya Elhilali. Characterization of noise contaminations in lung sound recordings. In *Engineering in Medicine and Biology Society*, volume 2013, pages 2551-4, 2013.

[7] B Flietstra, N Markuzon, A Vyshedskiy, and R Murphy. Automated analysis of crackles in patients with interstitial pulmonary fibrosis. *Pulmonary medicine*, 2011(2): 590506.

[8] D. Flores-Tapia, Z. M. K. Moussavi, and G. Thomas. Heart sound cancellation based on multiscale products and linear prediction. *Biomedical Engineering, IEEE Transactions on*, 54(2):234-243, February 2007.

[9] F. Ghaderi, H. R. Mohseni, and S. Sanei. Localizing heart sounds in respiratory signals using singular spectrum analysis. *Biomedical Engineering, IEEE Transactions on*, 58(12):3360-67, December 2011.

[10] J. Gnitecki, I. Hossain, H. Pasterkamp, and Z. Moussavi. Qualitative and quantitative evaluation of heart sound reduction from lung sound recordings. *Biomedical Engineering, IEEE Transactions on*, 52(10):1788-1792, October 2005.

[11] Kalpalatha K Guntupalli, Philip M Alapat, Venkata D Bandi, and Igal Kushnir. Validation of automatic wheeze detection in patients with obstructed airways and in healthy subjects. *The Journal of asthma: official journal of the Association for the Care of Asthma*, 45(10):903-7, December 2008.

[12] JohnsHopkinsHospital, Kristin Arcara, and Megan Tschudy. *The Harriet Lane Handbook: Mobile Medicine Series—Expert Consult*. Elsevier Mosby, Philadelphia, 19 edition, 2011.

[13] Yasemin P Kahya, Mete Yeginer, and Bora Bilgic. Classifying respiratory sounds with different feature sets. In *Engineering in Medicine and Biology Society*, volume 1, pages 2856-9, January 2006.

[14] A Kandaswamy, C Sathish Kumar, Rm Pl, and S Jayaraman. Neural classification of lung sounds using wavelet coe cients. *Computers in biology and medicine*, 34:523-537, 2004.

[15] Yasmina Kheddache and Chakib Tadj. Acoustic measures of the cry characteristics of healthy newborns and newborns with pathologies. *Journal of Biomedical Science and Engineering*, 06(08):796-804, 2013.

[16] Dror Lederman. Estimation of Infants' Cry Fundamental Frequency using a Modified SIFT algorithm. *Time*, pages 703-709, 2010.

[17] Shin Miura, Hirofumi Nakajima, Shigeki Miyabe, Shoji Makino, Takeshi Yamada, and Kazuhiro Nakadai. Restoration of clipped audio signal using recursive vector projection. *TENCON 2011-2011 IEEE Region 10 Conference*, pages 394-397, November 2011.

[18] Ram Mor, Igal Kushnir, Jean-Jacques Meyer, Joseph Ekstein, and Issahar Ben-Dov. Breath sound distribution images of patients with pneumonia and pleural effusion. *Respiratory care*, 52(12):1753-60, December 2007.

[19] Myung K Park. *Pediatric cardiology for practitioners*. Mosby Inc., Philadelphia, 3 edition, 1996.

[20] J C Pesquet, Hamid Krim, and Hervé Carfantan. Time-invariant orthonormal wavelet representations. *IEEE Transactions on Signal Processing*, 44(8):1964-1970, 1996.

[21] Sandra Reichert, Raymond Gass, Christian Brandt, and Emmanuel Andrès. Analysis of respiratory sounds: state of the art. *Clinical medicine. Circulatory, respiratory and pulmonary medicine*, 2:45-58, January 2008.

[22] R. J. Riella, P. Nohama, and J. M. Maia. Method for automatic detection of wheezing in lung sounds. *Braz J Med Biol Res*, 42(7):674-684, July 2009.

[23] A R A Sovijärvi, J Vanderschoot, and J E Earis. Standardization of computerized respiratory sound analysis. *European Respiratory Review*, 10(77):585, 2000.

[24] Styliani A Taplidou, Leontios J Hadjileontiadis, Ilias K Kitsas, et al. On applying continuous wavelet transform in wheeze analysis. *Conference Proceedings of the International Conference of IEEE Engineering in Medicine and Biology Society*, 5:3832-3835, 2004.

[25] L R Waitman, K P Clarkson, J A Barwise, and P H King. Representation and classification of breath sounds recorded in an intensive care setting using neural networks. *Journal of Clinical Monitoring and Computing*, 16(2):95-105, 2000.

[26] Philip Sanford Zeskind, Matthew S McMurray, Kristin a Garber, Juliana M Neuspiel, Elizabeth T Cox, Karen M Grewen, Linda C Mayes, and Josephine M Johns. Development of translational methods in spectral analysis of human infant crying and rat pup ultrasonic vocalizations for early neurobehavioral assessment. *Frontiers in psychiatry*, 2(October):56, January 2011.

[27] Rajkumar Palaniappan, Kenneth Sundaraj, and Sebastian Sundaraj, "A comparative study of the svm and k-nn machine learning algorithms for the diagnosis of respiratory pathologies using pulmonary acoustic signals," Bmc Bioinformatics, vol. 15, 2014

[28] Davis S, Mermelstein P. Comparison of parametric representations for monosyllabic word recognition in continuously spoken sentences. Acoustics, Speech and Signal Processing, IEEE Transactions on 1980; 28(4):357-366.

[29] Jin, F.; Sattar, F. & Goh, D. Y. T. (2014), 'New approaches for spectro-temporal feature extraction with applications to respiratory sound classification.', *Neurocomputing* 123, 362-371.

The embodiments illustrated and discussed in this specification are intended only to teach those skilled in the art how to make and use the invention. In describing embodiments of the invention, specific terminology is employed for the sake of clarity. However, the invention is not intended to be limited to the specific terminology so selected. The above-described embodiments of the invention may be modified or varied, without departing from the invention, as appreciated by those skilled in the art in light of the above teachings. It is therefore to be understood that, within the scope of the claims and their equivalents, the invention may be practiced otherwise than as specifically described.

We claim:

1. A digital electronic stethoscope, comprising:
an acoustic sensor assembly comprising a body sensor portion and an ambient sensor portion, said body sensor portion being configured to make acoustically coupled contact with a subject while said ambient sensor portion is configured to face away from said body sensor portion so as to capture environmental noise proximate said body sensor portion;
a signal processor and data storage system configured to communicate with said acoustic sensor assembly so as to receive detection signals therefrom, said detection signals comprising an auscultation signal comprising body target sound and a noise signal; and
an output device configured to communicate with said signal processor and data storage system to provide at least one of an output signal or information derived from said output signal,
wherein said signal processor and data storage system comprises a noise reduction system that removes both stationary noise and non-stationary noise from said detection signal to provide a clean auscultation signal substantially free of distortions,
wherein said signal processor and said data storage system further comprises an auscultation sound classification system configured to receive said clean auscultation signal and provide a classification thereof as at least one of a normal breath sound or an abnormal breath sound, and
wherein said noise reduction system suppresses ambient noise by multiband spectral subtraction of said noise signal from said detection signal to provide said clean auscultation signal substantially free of distortions.

2. The digital electronic stethoscope according to claim 1, wherein said body sensor portion of said acoustic sensor assembly comprises a microphone array of a plurality of microphones.

3. The digital electronic stethoscope according to claim 2, wherein said each of said plurality of microphones is an electret microphone.

4. The digital electronic stethoscope according to claim 1, wherein said output device is at least one of earphones, a smart phone, or a computer.

5. The digital electronic stethoscope according to claim 1, wherein said noise reduction system comprises a clipping repair system to repair clipping of said auscultation signal to provide said clean auscultation signal substantially free of distortions.

6. The digital electronic stethoscope according to claim 1, wherein said noise reduction system comprises a heart sound elimination system to remove said subject's heart sounds from said detection signal to provide said clean auscultation signal substantially free of distortions.

7. The digital electronic stethoscope according to claim 1, wherein said noise reduction system comprises a friction noise removal system to remove friction noise of said acoustic sensor assembly rubbing against said subject from said detection signal to provide said clean auscultation signal substantially free of distortions.

8. The digital electronic stethoscope according to claim 6, wherein said noise reduction system comprises a friction noise removal system to remove friction noise of said acoustic sensor assembly rubbing against said subject from said detection signal to provide said clean auscultation signal substantially free of distortions.

9. The digital electronic stethoscope according to claim 1, wherein said noise reduction system comprises a subject's crying removal system to remove said crying noise of said subject from said detection signal to provide said clean auscultation signal substantially free of distortions.

10. The digital electronic stethoscope according to claim 7, wherein said noise reduction system comprises a subject's crying removal system to remove said crying noise of said subject from said detection signal to provide said clean auscultation signal substantially free of distortions.

11. The digital electronic stethoscope according to claim 8, wherein said noise reduction system comprises a subject's crying removal system to remove said crying noise of said subject from said detection signal to provide said clean auscultation signal substantially free of distortions.

12. The digital electronic stethoscope according to claim 1, wherein said auscultation sound classification system is a machine learning system that learns from training data.

13. The digital electronic stethoscope according to claim 11, wherein said auscultation sound classification system uses a binary support vector machine (SVM) algorithm and radial-basis kernels (RBFs).

14. The digital electronic stethoscope according to claim 1, wherein said multiband spectral subtraction includes:
processing individual frequency bands based on spectral characteristics of a target body sound and said noise signal,
adjusting processing of a localized time window of said detection signal based on local Signal To Noise Ratio (SNR) information to provide a processed signal, and
smoothing said processed signal along adjacent time frames and frequency bands to reduce reconstruction distortions in said processed signal.

15. A method of processing signals detected by a digital electronic stethoscope, comprising:
obtaining an auscultation signal from said electronic stethoscope, said auscultation signal comprising a target body sound;
obtaining a noise signal comprising noise from an environment of said body;
obtaining a processed signal by reducing unwanted noise in said auscultation signal based on at least one of said auscultation signal and said noise signal;
performing acoustic analysis of said processed signal; and
performing statistical analysis of said processed signal,
wherein said obtaining said processed signal includes suppressing ambient noise by multiband spectral subtraction of said noise signal from said auscultation signal.

16. The method of processing signals according to claim 15, wherein said obtaining said processed signal includes detecting and repairing clipping distortion in said auscultation signal.

17. The method of processing signals according to claim 15, wherein said multiband spectral subtraction includes:
processing individual frequency bands based on spectral characteristics of said target body sound and said noise signal,
adjusting the processing of a localized time window of said auscultation signal based on local Signal To Noise Ratio (SNR) information, and
smoothing said processed signal along adjacent time frames and frequency bands to reduce reconstruction distortions in said processed signal.

18. The method of processing signals according to claim 15, wherein said obtaining said processed signal includes reducing mechanical noise of said electronic stethoscope.

19. The method of processing signals according to claim 15, wherein said obtaining said processed signal includes suppressing noise from crying of a patient from whom said auscultation signal was obtained.

20. The method of processing signals according to claim 15, wherein said obtaining said processed signal includes:
identifying and suppressing or extracting heart sounds in said auscultation signal, and
extrapolating said processed signal across intervals where said heart sounds were suppressed or extracted using an auto-regressive/moving average (ARMA) method.

21. The method of processing signals according to claim 15, wherein said acoustic analysis includes:
obtaining an auditory spectrogram by enhancing said processed signal using a plurality of filters, and
capturing signal modulations along both time and frequency axes of said auditory spectrogram.

22. The method of processing signals according to claim 15, wherein said statistical analysis includes classification of sounds obtained from said auscultation signal using binary support vector machines (SVMs) and radial-basis kernels (RBFs).

23. A computer-readable medium comprising non-transitory computer-executable code for processing signals detected by a digital electronic stethoscope, which when executed by a computer causes the computer to:
obtain an auscultation signal from said electronic stethoscope, said auscultation signal comprising a target body sound;
obtain a noise signal comprising noise from an environment of said body;
obtain a processed signal by reducing unwanted noise in said auscultation signal based on at least one of said auscultation signal and said noise signal;
performing acoustic analysis of said processed signal; and
performing statistical analysis of said processed signal,
wherein said obtaining said processed signal includes suppressing ambient noise by multiband spectral subtraction of said noise signal from said auscultation signal.

24. The computer-readable medium according to claim 23, wherein said obtaining said processed signal includes detecting and repairing clipping distortion in said auscultation signal.

25. The computer-readable medium according to claim 23, wherein said multiband spectral subtraction includes:
processing individual frequency bands based on spectral characteristics of said target body sound and said noise signal,
adjusting the processing of a localized time window of said auscultation signal based on local Signal To Noise Ratio (SNR) information, and
smoothing said processed signal along adjacent time frames and frequency bands to reduce reconstruction distortions in said processed signal.

26. The computer-readable medium according to claim 23, wherein said obtaining said processed signal includes reducing mechanical noise of said electronic stethoscope.

27. The computer-readable medium according to claim 23, wherein said obtaining said processed signal includes suppressing noise from crying of a patient from whom said auscultation signal was obtained.

28. The computer-readable medium according to claim 23, wherein said obtaining said processed signal includes:
identifying and suppressing or extracting heart sounds in said auscultation signal, and
extrapolating said processed signal across intervals where said heart sounds were suppressed or extracted using an auto-regressive/moving average (ARMA) method.

29. The computer-readable medium according to claim 23, wherein said acoustic analysis includes:
obtaining an auditory spectrogram by enhancing said processed signal using a plurality of filters, and
capturing signal modulations along both time and frequency axes of said auditory spectrogram.

30. The computer-readable medium according to claim 23, wherein said statistical analysis includes classification of sounds obtained from said auscultation signal using binary support vector machines (SVMs) and radial-basis kernels (RBFs).

* * * * *